United States Patent [19]

Saito et al.

[11] Patent Number: 5,785,835
[45] Date of Patent: Jul. 28, 1998

[54] ELECTROPHORESIS METHOD AND DEVICES

[75] Inventors: Katsuyuki Saito, Agoura; Stewart Han; Jar-How Lee, both of Los Angeles, all of Calif.

[73] Assignee: One Lambda, Canoga Park, Calif.

[21] Appl. No.: 631,406

[22] Filed: Apr. 12, 1996

[51] Int. Cl.$^6$ .................. G01N 27/26; G01N 27/447
[52] U.S. Cl. .................. 204/616; 204/456; 204/466; 204/606
[58] Field of Search .................. 204/606, 607, 204/608, 609, 610, 612, 613, 614, 615, 616, 617, 618, 619, 620, 621, 456, 466

[56] References Cited

U.S. PATENT DOCUMENTS

| | | | |
|---|---|---|---|
| 4,294,684 | 10/1981 | Serwer | 204/620 X |
| 4,443,319 | 4/1984 | Chait et al. | 204/616 |
| 5,045,164 | 9/1991 | Tansamrit et al. | 204/616 X |
| 5,399,255 | 3/1995 | Sarrine | 204/616 |

FOREIGN PATENT DOCUMENTS 2 284 484   6/1995   United Kingdom.

*Primary Examiner*—Bruce F. Bell
*Assistant Examiner*—John S. Starsiak, Jr.
*Attorney, Agent, or Firm*—Marshall, O'Toole, Gerstein, Murray & Borun

[57] ABSTRACT

The present invention is directed to methods and apparatus for simultaneous gel electrophoresis analysis of multiple nucleic acid samples. The invention provides an electrophoresis gel-matrix layer having two mutually opposite ends for application of an electrophoresis voltage thereto, an exposed major surface extending between the two ends, and a plurality of wells in the thickness of the layer and open at said exposed surface, wherein the wells are arranged in a plurality of rows each extending transversely of the end-to-end direction of the layer and wherein the wells in successive rows are aligned with each other so as to form columns which are aligned in the end-to-end direction said gel-matrix layer further comprising two slots positioned at opposing ends of the plurality of open sample wells for insertion of electrophoresis electrodes.

13 Claims, 4 Drawing Sheets

ELECTROPHORESIS METHOD AND DEVICES

BACKGROUND OF THE INVENTION

The present invention relates to methods and apparatus for gel electrophoresis analysis of nucleic acids. More specifically, the invention relates to improved methods for analysis of deoxyribonucleic acid (DNA) useful for tissue typing such as for human leukocyte antigen typing.

Those engaged in laboratory identification and manipulation of DNA commonly employ the polymerase chain reaction method (PCR) to amplify a particular segment of DNA. During this process, a distinct size of DNA fragment is generated. Typically, the process is carried out in a microcentrifuge tube that holds from 0.2 to 0.7 milliliter (mL) volume of liquid. For a large number of samples, a microtiter plate or Terasaki tray (One Lambda, Canoga Park, Calif.) containing dozens of well (60, 72, 96, 384 and the like) may be used. The resulting PCR products are typically analyzed on a gel-matrix layer using an electrophoresis method. In this method, PCR products are first transferred individually from original reaction tubes to a gel-matrix. Conventional electrophoresis methods involve the placement of a gel-matrix layer on the bottom of a electrophoresis chamber which is then filled with as much as several hundred mL of electrophoresis buffer solution to immerse the gel-matrix layer. An electrophoresis current is applied to electrodes placed in the solution bath on opposing sides of the gel-matrix layer causing the DNA fragments to migrate toward the positive electrode. The migration speed of the DNA fragments depends on their size such that the larger the size of a DNA fragment, the slower is its speed of migration through the gel-matrix. The gel-matrix is then soaked in a solution containing a DNA-chelating fluorescent dye such as ethidium bromide which specifically binds DNA for visualization as a pattern of bands under an ultraviolet light source. Alternatively, the DNA-chelating dye can be incorporated into the gel.

These electrophoresis methods allow one to detect and measure the size of DNA fragments generated in PCR. When these methods are performed on a large number of PCR products the worker must manually transfer each sample from the reaction vessels to the corresponding wells in a gel-matrix in an orderly and consistent manner. Because of the complicated nature of this process, there is a desire for systems and methodologies which will minimize the chance for errors occurring due to sample mishandling including cross-contamination, loss and transfer error. Moreover, because conventional methods of electrophoresis utilize large quantities of potentially toxic electrophoresis buffer there also exists a desire for systems and methodologies with improved efficiencies and which minimize disposable waste.

Of interest to the present invention is the gel-matrix device described in University College London, UK Patent Application GB 2,284,484 which is directed to an electrophoresis gel-matrix layer comprising a well matrix offset from the axis of electrophoresis current flow. The application describes the system wherein the electrophoresis tracks obtained from wells of one row will pass, if extended so far, between wells of at least one other row and tracks obtained therefrom. This feature provides the possibility of higher resolution by elongation of the electrophoresis tracks but may be difficult to read because extension of the electrophoresis tracks causes tracks from two, three or more sample rows to lie adjacent one another thus confusing their interpretation. Moreover, the system is inefficient because the offset gels are large, must be run in oversized specially made gel boxes using elongated electrodes and use large quantities of electrolyte. Accordingly, there remains a need in the art for electrophoresis systems for simultaneous analysis of large numbers of samples which can be easily read and remain simple and efficient.

SUMMARY OF THE INVENTION

The present invention relates to methods and apparatus for simultaneous gel electrophoresis analysis of multiple nucleic acid samples including PCR products. The electrophoresis gel-matrix layers of the invention provide improvements in analysis of multiple nucleic acid samples. Specifically, the apparatus comprises an electrophoresis gel-matrix layer having two mutually opposite ends for application of an electrophoresis voltage thereto, an exposed major surface extending between the two ends, and a plurality of wells in the thickness of the layer and open at said exposed surface, wherein the wells are arranged in a plurality of rows each extending transversely of the end-to-end direction of the layer and wherein the wells in successive rows are aligned with each other so as to form columns aligned in the end-to-end direction.

According to one particularly preferred aspect of the invention, the gel-matrix layer comprises two slots positioned at opposing ends of the plurality of open sample wells for insertion of electrophoresis electrodes. Most preferably the slots are adjacent opposite ends of the gel-matrix layer. The gel-matrix layers of the invention comprising such slots for insertion of the electrophoresis electrodes may are particularly useful as they may be used to carry out a method of "dry" electrophoresis. Thus, instead of immersing electrodes in a bath of electrophoresis buffer containing the gel-matrix layer, the bath is eliminated, a relatively small amount electrophoresis buffer is added directly to the gel-matrix layer and the electrodes are inserted into the slots in the gel-matrix layer.

According to a further aspect of the invention, an improved comb for forming sample wells in an electrophoresis gel-matrix layer is provided. Use of the combs further provides improved electrophoresis gel-matrix layers comprising sample wells produced by means of the improved combs. Further, improved methods of carrying out electrophoresis are provided comprising use of gel-matrix layers produced by means of the combs. The combs of the invention comprise one or more teeth for sample well formation which are tapered by means of a bevel cut on the side of the teeth facing away from the direction of electrophoresis flow such that the thickness at the tip of the teeth is from about 10% to about 60%, and preferably less than 50% that of the thickness at the base of the teeth. By providing the bevel cut on the side of the comb teeth directed away from the direction of electrophoresis transport a flat "front" is provided ensuring that sample DNA at different vertical levels within the sample well start at the same horizontal location with respect to the flow toward the positively charged electrode. This aspect of the invention minimizes blurring of the electrophoresis bands and provides improved resolution to the electrophoresis devices thus allowing shortening of the electrophoresis transport distance required to achieve a given separation result.

The comb teeth are preferably tapered by means of a bevel cut at an angle of from 20° to 40°, and most preferably about 30° from the plane of the comb. The comb teeth provide improvements in electrophoresis resolution by minimizing the effects of diffusion which occurs between the time of addition of sample to a sample well and application of an electrophoresis voltage. The effects of such diffusion become more pronounced in cases where multiple samples or multiple rows of samples are run on single gel-matrix layers such as those of the invention where sample addition might be extremely time consuming and there might be a prolonged time between addition of a first sample and application of the electrophoresis voltage. Use of the improved combs of the invention helps provide improved resolution of the electrophoresis results thus making possible the methods and apparatus of the invention for simultaneous gel electrophoresis analysis of multiple samples in a compact device.

The invention also provides a method of carrying out simultaneous electrophoresis of multiple samples using the improved gel-matrix layers of the invention, comprising the steps of: (1) providing an electrophoresis gel-matrix layer having two mutually opposite ends for application of an electrophoresis voltage thereto, an exposed major surface extending between the two ends, and a plurality of wells in the thickness of the layer and open at said exposed surface, wherein the wells are arranged in a plurality of rows each extending transversely of the end-to-end direction of the layer and wherein the wells in successive rows are aligned with each other in the end-to-end direction, said gel-matrix layer further comprising two slots positioned at opposing ends of the plurality of open sample wells, (2) placing each sample in one of each respective well, (3) subjecting all the samples to electrophoresis by applying a voltage in a direction, along the layer of gel material such that the electrophoresis track of each sample will encounter, if sufficiently extended, the well in the next adjacent row, and (4) halting application of the voltage prior to transport of each sample to the well in the next adjacent row.

DETAILED DESCRIPTION OF THE INVENTION

Figure 1:
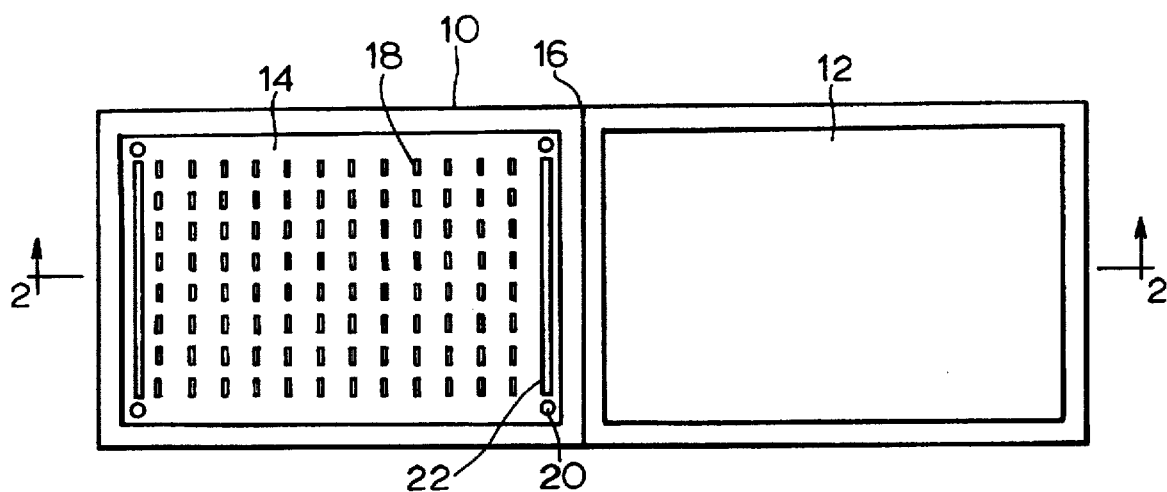
FIG. 1 depicts top view of a gel casting case for forming the gel-matrix layers of the invention.

The methods and apparatus of the invention provide a semi-automated system for electrophoretic separation of large numbers of nucleic acid samples and are particularly useful for typing human leukocyte antigen (HLA) gene samples produced using nucleic acid amplification methods. As such the gel-matrix layers are capable of achieving a resolution of about 400 base pairs or less for DNA fragments less than 1000 base pairs in length over an electrophoresis distance of 0.8 cm or less. In other words, the gel-matrix layers are capable of distinguishing between DNA "typing" fragments 90 to 300 base pairs in length and DNA "control" fragments 700 to 800 base pairs in length as used in HLA typing assays over an electrophoresis distance of 0.8 cm or less. The gel-matrix layers of the invention thus provide a clear indication of positive or negative results based on the presence or absence of DNA bands. The system can be used for any electrophoresis method that requires short DNA migration distances such as "± PCR reaction analysis."

According to methods of practicing the invention, electrophoresis distances of 0.8 cm and as small as 0.5 cm, depending on variation of the % w/v concentration of agarose or other gel according to the skill in the art, would provide sufficient resolution for analysis of HLA typing using nucleic acid amplification system (usually referred to as PCR-SSP for sequence-specific-primer). Typically, HLA typing only requires distinguishing two DNA fragments with lengths of 90 to 300 base pairs from fragments 500 to 1000 base pairs in length. As long as resulting amplified DNA fragments are within those two lengths, they can be separated and identified according to the present invention in embodiments wherein the distance between rows of sample wells is 0.8 cm which corresponds to the spacing of a 12 row by 8 column standard 96 well microtiter tray. The apparatus of the invention can be used to carry out electrophoresis of other nucleic acid fragments by adjustment of the % w/v concentration of the gel matrix and by allowing the nucleic acids to migrate over greater distances using fewer numbers of combs.

The methods and apparatus provide a substantial increase in throughput and accuracy in the analysis of large number of nucleic acid samples. Moreover, the gel-matrix layers of the invention are particularly useful in automated systems for sample transfer and analysis including those using automatic liquid aspiration and dispensing devices. Using an automatic liquid aspiration/dispensing device the invention provides simultaneous transfer of either 8 or 12 samples using a multichannel pipette, or all 96 (or other number of samples) using a 96 well transfer device such as is known in the art.

Unlike conventional electrophoresis, samples may be electrophoresed in a gel-matrix layer which contains as little as 10 mL of electrophoresis buffer solution. Conventional electrophoresis methods involve the placement of a gel-matrix layer on the bottom of a electrophoresis chamber which is then filled with as much as several hundred milliliters of electrophoresis buffer solution to immerse the gel-matrix layer. Electrodes for transmission of the electrophoresis current are placed in the solution bath on opposing ends of the gel-matrix layer. The method of the invention places the electrophoresis electrodes directly into the gel-matrix layer which has been "wetted" with electrophoresis buffer and avoids the need for a large quantity of electrophoresis buffer to immerse the gel-matrix layer and electrodes. Consequently, the method of the invention uses significantly less electrophoresis solution than conventional methods (as little as one-thirtieth the amount) using a gel box and also minimizes the quantity of disposable waste and the risk of contamination therewith.

The apparatus of the present invention comprises an electrophoresis gel-matrix layer having two mutually opposite ends for application of an electrophoresis voltage thereto, an exposed major surface extending between the two ends, and a plurality of wells in the thickness of the layer and open at said exposed surface, wherein the wells are arranged in a plurality of rows each extending transversely of the end-to-end direction of the layer and wherein the wells in successive rows are aligned with each other so as to form columns which are aligned in the end-to-end direction.

A preferred gel-matrix layer according to the invention consists of a 2 inch by 4 inch polystyrene tray that contains an agarose matrix containing a plurality of wells for deposit of samples to be analyzed. The agarose matrix is preferably 5 mm thick and according to one embodiment the wells are approximately 1 mm wide by 3 mm deep by 5 mm long and each hold approximately 10–20 microliters of volume. While the wells are approximately 1 mm wide at their tops, they are about 0.5 mm wide at their bottoms as will be discussed later. The number and positions of wells preferably correspond to the configuration of reaction vessels used for nucleic acid amplification in order to promote ease of sample transfer. For example, when the gel-matrix layers of the invention are to be used with standard Terasaki trays (One Lambda, Canoga Park, Calif.) having 72 wells, the wells in the gel-matrix are positioned such that a row of six wells with a spacing of 3 mm is placed across the two inch width of the tray, and 12 such rows are formed with a spacing of 8 mm between each row. This configuration of well positions matches exactly the well positions of a standard 72 well Terasaki tray and allows for ease of transfer or sample reagents according to various methods. Other configurations, including standard 96 well configurations such as are commercially available as MicroAmp 9600 Tray/Retainer Set (Perkin Elmer, Part No. N801-0531) can also be used. Such a tray accommodates PCR reaction tubes such as MicroAmp 8 strip reaction tubes (Perkin Elmer, Part No. N801-0580). This strip of 8 reaction tubes corresponds to one column of wells in the 96 well configuration of the invention. The gel-matrix layers including the gel cast and gel tray box described herein can be used for analysis of standard 96 well sample trays when samples can be analyzed in an electrophoresis distance of 0.8 cm or less. For analysis of a smaller number of samples requiring longer separation distance, a gel can be made using fewer combs creating more space between sample wells and allowing a longer electrophoresis distance.

The sample wells in the gel-matrix containing layers are preferably formed by the process of molding agarose or other gel-matrix substrate around combs whose teeth define wells in the solidified gel. According to a preferred aspect of the invention, the comb teeth are designed in a manner to minimize the bulky appearance of resulting nucleic acid bands due to a diffusion of sample through the gel-matrix prior to electrophoresis. Specifically, the comb teeth are of constant width but are tapered by means of a bevel cut on the side of the teeth facing away from the direction of electrophoresis flow such that the thickness at the tip is approximately half that at the base of the teeth. The side of the comb teeth facing in the direction of electrophoresis transport is therefore preferably perpendicular to the surface of the gel matrix layer and thus normal to the direction of electrophoresis flow. This orientation minimizes diffusion of sample within the wells prior to application of an electrophoresis voltage and provides the advantage of higher resolution DNA bands in electrophoresis gel-matrix layers comprising multiple rows of wells. This is particularly the case where electrophoresis gel-matrix layers comprise multiple rows of sample wells such as those of the invention which can result in an elongated period of time between introduction of the first sample into one sample well or row of sample wells and the introduction of sample into the last sample well and application of the electrophoresis current.

Figure 5:
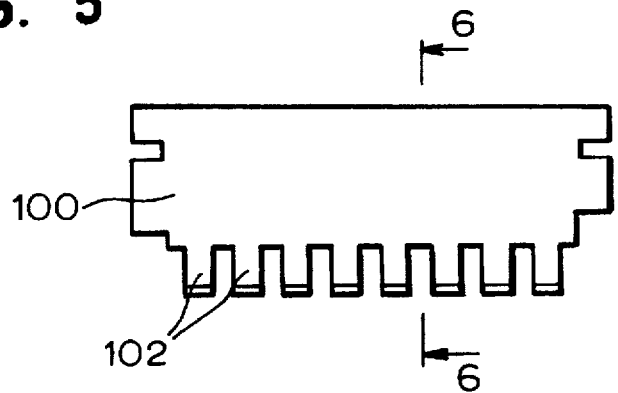
FIG. 5 depicts a preferred comb for use in forming the gel-matrix layers of the invention.
Figure 6:
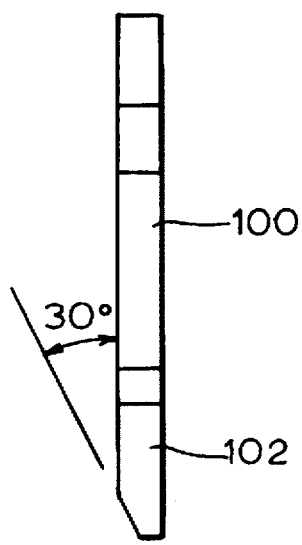
FIG. 6 depicts a cross-section of the preferred comb of FIG. 5.

As a result, sample wells in the gel-matrix have a wide enough opening to accommodate standard disposable pipette tips in a pipetting device, yet have a bottom thin enough to create sharp DNA bands for clear-cut interpretation of results. Thus according to one embodiment of the invention, (See FIGS. 5 and 6) a comb (100) is fabricated from acrylic stock 0.080 inches (~2 mm) thick with teeth (102) measuring 0.20 (~5 mm) inches wide and 0.370 inches long. The ends of the teeth are bevel cut at their midthickness along a 30° angle from the plane of the acrylic stock such that the edge of the teeth have a thickness of 0.040 inches.

The gel-matrix layer is then formed around combs defining successive rows of sample wells by pouring a gel substrate material in liquid form into a gel casting case or gel box. While preferred gel-matrix layers are 2 to 5 mm thick, gels up to 2 cm and thicker can be produced according to the invention. While agarose at w/v concentrations of 2–2.5% is the preferred gel-matrix material for use in preparing devices according to the invention, other materials known to the art may also be used including acrylamide gel. After the gel substrate material has hardened, the combs may be removed leaving a plurality of sample wells in multiple rows wherein the sample wells assume the shape of the comb teeth.

According to one method of transfer, a multichannel pipette device having a row of pipette tubes corresponding to a row of sample wells in a microtiter well tray are used to transfer sample from rows of wells on the microtiter well tray to corresponding successive rows of wells on the gel-matrix tray. Alternatively, the gel-matrix layer can be placed upside down on top of the PCR microtiter tray such that the microtiter wells correspond to the empty gel wells on the gel-matrix tray. By centrifuging this tray-to-tray configuration with the empty tray facing outside of the centrifuge, the contents of the PCR tray wells can be transferred into the detection gel-matrix layer sample wells. Such transfers can be facilitated by providing the lid of the gel-matrix tray with funnel-like wells to direct sample into appropriate wells.

According to another aspect of the invention, the need to use a specialized electrophoresis chamber to apply an electrical current to the gel-matrix is eliminated. In conventional methods of gel electrophoresis, a gel-matrix is separately prepared on glass plates or in between two glass plates. The formed gel-matrix is then placed in an apparatus containing a large volume of electrophoresis buffer solution which is typically a commercially available solution comprising Trizma base, boric acid, disodium EDTA and deionized water (TBE solution). According to this method of the invention, electrodes may be embedded on both ends of the gel-matrix tray or alternatively, troughs into which electrodes may be inserted are formed at both ends of the gel-matrix tray. A small amount, preferably 10 mL, of TBE buffer solution is then applied to the gel-matrix tray and electrophoresis can be carried out within the tray without the need of transferring a gel-matrix to another apparatus or immersing the gel-matrix in an electrophoresis solution as practiced by the prior art. Electrophoresis is carried out by applying an electrophoresis current along the length of the gel thus causing nucleic acids within the samples to move in the direction of the current. According to one embodiment of the invention, the current is stopped in time to achieve a resolution of 400 base pairs or less for DNA fragments less than 1000 base pairs in length but prior to the time when the DNA would reach the next well in the end-to-end direction of the gel-matrix layer. The specific electrophoresis distance required to achieve a resolution of 400 base pairs or less for DNA fragments less than 1000 base pairs in length is dependent upon the % w/v concentration of the gel-matrix layer but for molecular biology grade agarose with a w/v concentration of 2.5% is less than 0.8 cm using sample wells formed with the preferred combs of the invention.

According to one aspect of the invention the gel-matrix can also comprise pre-mixed fluorescent dye that specifically stains nucleic acids. This allows visualization of separated DNA immediately after the completion of electrophoresis without removal of the gel-matrix.

Other aspects and advantages of the present invention will be understood upon consideration of the following illustrative examples.

EXAMPLE 1

Figure 2:
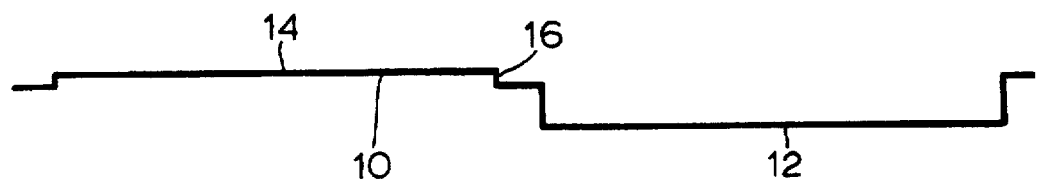
FIG. 2 depicts a side view of a gel casting case for forming the gel-matrix layers of the invention.

According to this example, a gel-matrix layer for conducting tissue typing according to the invention is prepared. FIGS. 1 and 2 depict a gel casting case (10) made of a plastic or other material which is transparent to ultra-violet radiation. The gel-matrix layers of the invention are formed in this case according to the method set out below. The gel casting case comprises a base portion (12) and a lid portion (14) which are attached by a hinge (16) such that the lid portion may be closed and sealed onto the base portion (12). The lid (14) contains an array of slits (18) which correspond to wells to be formed within the gel-matrix layer. The lid (14) also contains one or more ports (20) for addition of liquid agarose or other gel-forming agent and release of air during filling. In addition, the lid (14) comprises two elongated slits (22) at opposite ends of the lid and extending substantially the width of the lid for insertion of electrophoresis electrodes.

Figure 3:
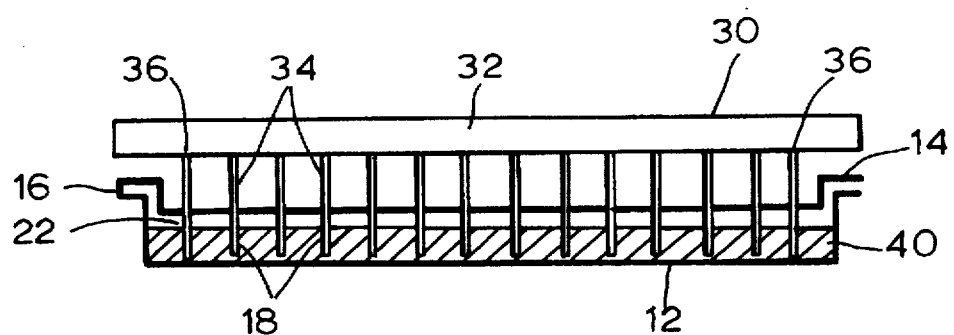
FIG. 3 depicts a method of forming a gel-matrix layer according to the invention wherein a comb is used to form sample and electrode wells.
Figure 4:
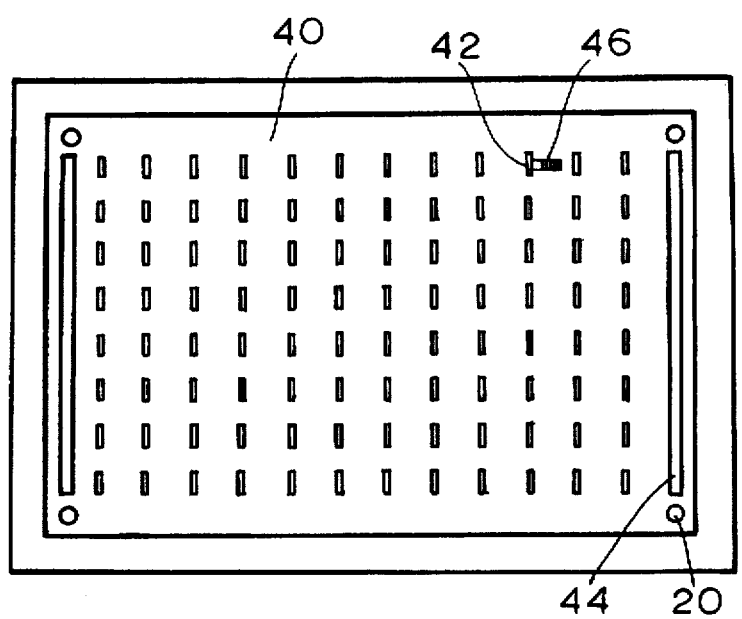
FIG. 4 depicts a top view of a gel-matrix layer according to the invention including a depiction of a gel track of DNA from one sample well.

FIGS. 3 and 4 disclose one method of preparing the gel-matrix layers of the invention wherein the lid (14) is closed over the base (12) of the gel casting case (10) and a multiple row comb (30) comprising a base (32), twelve comb elements (34) having multiple teeth, and two transverse projections (36) is fitted through the lid (14) such that a tooth from each comb (34) is fitted through each slit (18) and further that a transverse projection (36) is fitted through each of the two elongated slits (22). The teeth from each comb (34) will define sample wells in the gel-matrix layer while the transverse projections (36) will define slots for insertion of electrophoresis electrodes.

Liquid agarose or other suitable gel is then introduced into the gel casting case (10) by means of one or more of the ports (20) and allowed to harden to form a gel-matrix layer (40) within the gel casting case. The multiple row comb (30) is then removed from the gel leaving a plurality of open sample wells (42) molded in the gel in the pattern of the teeth of the comb as well as two slots (44) positioned at opposing sides of the plurality of open sample wells and most preferably adjacent opposite ends of the gel-matrix layer for insertion of electrophoresis electrodes. About 10 mL of TBE electrophoresis buffer solution is then added to the trays followed by sealing of the tray with an airtight heat sealable film. The gel-matrix layer may now be used or stored for later use.

EXAMPLE 2

According to this example, the gel-matrix layer prepared according to the method of Example 1 is used to conduct HLA tissue typing of PCR samples. PCR samples are preferably aspirated from PCR reaction vessels by means of a multichannel pipette device having pipettes corresponding dimensional to both the multiwell tray containing the PCR vessels as well as to the plurality of wells on the gel-matrix layer. Thus, for example, where the PCR reaction is carried out in a 96 well tray, the samples are transferred by means of a 96 channel pipette corresponding dimensional to the tray such that all of the samples may be aspirated simultaneously by the pipette device. The pipette device is then used to deposit the 96 separate samples into corresponding sample wells (42) of the gel-matrix layer such that the arrangement of samples in the gel-matrix layer wells corresponds to that of the samples in the PCR reaction tray.

The pipette device is removed from the gel-matrix layer and electrodes are then inserted through the lid of the gel casting case into the slots (44). Electric current is then applied to carry out the electrophoresis process wherein the samples are transported in the direction of the electric field along tracks (46). The current is shut off prior to the time when the nucleic acid samples encounter the wells of the next successive row. Ultra-violet light is used to detect the location of the transported nucleic acids by means of the fluorescent DNA chelating dye and the gel is "read" and/or photographed accordingly. The devices of the present invention are particularly useful because the wells in the gel-matrix layer on which the DNA samples are imaged correspond exactly to those on the microtiter well plates containing the PCR samples thus providing ease of analysis.

EXAMPLE 3

Figure 7:
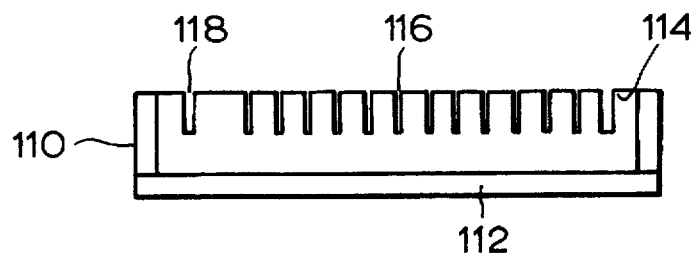
FIG. 7, FIG. 8 and FIG. 9 depict side views of an alternative gel tray box and methods of its use according to the invention.
Figure 8:
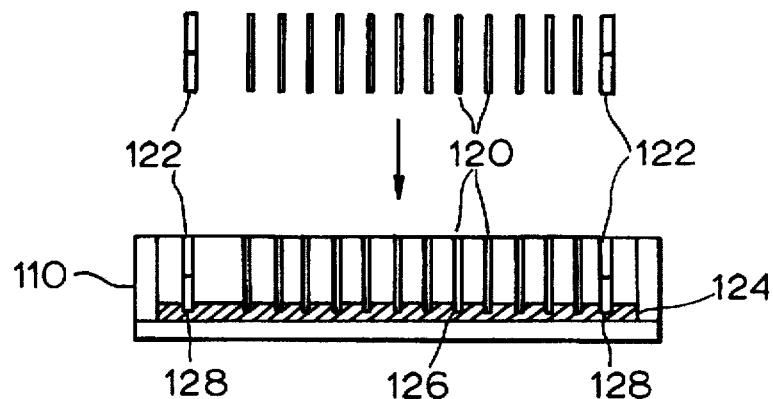
Figure 9:
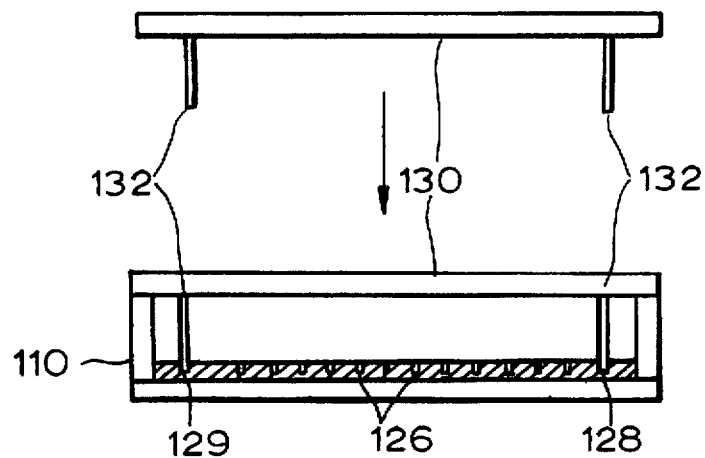

According to this example, gel-matrix layers according to the invention may also be formed in reusable gel tray boxes (110) as disclosed in FIGS. 7, 8 and 9 which comprise a rectangular base transparent to ultra-violet light (112), and sides along the major dimension (114) defining twelve openings (116) for fitting of combs and two major openings (118) at either end of the side for fitting of elongated projections. According to a method of preparing the gel-matrix layers of the invention twelve combs (120) each comprising eight teeth (similar to that of FIG. 5) are inserted into the openings (116) in the sides of the gel tray box along with two elongated projections (122) which fit into the major openings (118). Liquid agarose is poured into the gel tray box and allowed to harden. The combs (120) defining sample wells and the elongated projections (122) defining electrode slots are removed to produce the gel-matrix layer (124) comprising a plurality of sample wells (126) and two electrode slots (128).

According to one method of practicing the invention, nucleic acid samples are added to the sample wells (126) of the gel-matrix layer and a lid (130) comprising electrodes (132) is placed on top of the gel tray box and an electrophoresis current applied. The current is shut off prior to the time when the nucleic acid samples encounter the wells of the next successive row and ultra-violet light is used to detect the location of the transported nucleic acids.

Numerous modifications and variations in the practice of the invention are expected to occur to those skilled in the art upon consideration of the presently preferred embodiments thereof. For example, a wide variety of alternative methods may be used to prepare the gel-matrix layers of the invention as would be apparent to those of skill in the art contemplating this disclosure. Consequently, the only limitations which should be placed upon the scope of the invention are those which appear in the appended claims.

What is claimed:

1. An electrophoresis gel-matrix layer having two mutually opposite ends for application of an electrophoresis voltage thereto, an exposed major surface extending between the two ends, and a plurality of wells in the thickness of the layer and open at said exposed surface, wherein the wells are arranged in a plurality of rows each extending transversely of the end-to-end direction of the layer and wherein the wells in successive rows are aligned with each other so as to form columns which are aligned in the end-to-end direction, said gel-matrix layer further comprising two slots positioned at opposing ends of the plurality of open sample wells for insertion of electrophoresis electrodes.

2. The gel-matrix layer of claim 1 wherein said slots are adjacent opposite ends of the gel-matrix layer.

3. The gel-matrix layer of claim 1 comprising electrodes for transmission of an electrophoresis current inserted in said slots.

4. The gel-matrix layer of claim 1 wherein the gel-matrix layer is agarose.

5. The gel-matrix layer of claim 1 which comprises electrophoresis buffer.

6. The gel-matrix layer of claim 1 wherein the successive rows are located 0.8 cm or less apart.

7. The gel-matrix layer of claim 1 having a direction of electrophoresis flow from one end to said opposite end wherein the sample wells are tapered such that the side in the direction of electrophoresis flow is perpendicular to the surface of the gel-matrix layer and the width of the bottom of the sample wells is from about 10% to about 60% that of the thickness at the top of the wells.

8. The gel-matrix layer of claim 1 which is capable of achieving a resolution of 400 base pairs or less for DNA fragments less than 1000 base pairs in length over an electrophoresis distance of 0.8 cm or less.

9. A method of carrying out simultaneous electrophoresis of multiple samples, comprising the steps of:

providing an electrophoresis gel-matrix layer having two mutually opposite ends for application of an electrophoresis voltage thereto, an exposed major surface extending between the two ends, and a plurality of wells in the thickness of the layer and open at said exposed surface, wherein the wells are arranged in a plurality of rows each extending transversely of the end-to-end direction of the layer and wherein the wells in successive rows are aligned with each other so as to form columns which are aligned with each other in the end-to-end direction said gel-matrix layer further comprising two slots positioned at opposing ends of the plurality of open sample wells for insertion of electrophoresis electrodes, placing each sample in one of each respective well, placing an electrophoresis electrode in each of said slots, and subjecting all the samples to electrophoresis by applying a voltage in a direction, along the layer of gel material such that the electrophoresis track of each sample will encounter, if sufficiently extended to the well in the next adjacent row and halting application of the voltage prior to transport of each sample to the well in the next adjacent row.

10. The method of claim 9 wherein the method achieves a resolution of 400 base pairs or less for DNA fragments less than 1000 base pairs in length over an electrophoresis distance of 0.8 cm or less.

11. The method of claim 9 wherein the method achieves a resolution sufficient for human leukocyte antigen typing.

12. The method of claim 9 wherein said gel-matrix layer comprises electrophoresis buffer.

13. The method of claim 9 wherein the gel matrix has a direction of electrophoresis flow from one end to said opposite end and wherein the sample wells are tapered such that the side in the direction of electrophoresis flow is perpendicular to the surface of the gel-matrix layer and the width of the bottom of the sample wells is from about 10% to about 60% that of the thickness at the top of the wells.

* * * * *